United States Patent [19]

Primm

[11] Patent Number: 4,957,669
[45] Date of Patent: Sep. 18, 1990

[54] METHOD FOR PRODUCING TUBING USEFUL AS A TAPERED VASCULAR GRAFT PROSTHESIS

[75] Inventor: Alfred E. Primm, Santa Ana, Calif.

[73] Assignee: Shiley, Inc., Irvine, Calif.

[21] Appl. No.: 334,313

[22] Filed: Apr. 6, 1989

[51] Int. Cl.5 .................. B06B 3/00; B29C 33/60; B29C 61/00
[52] U.S. Cl. .................. 264/23; 264/68; 264/130; 264/230; 264/288.8; 264/289.6; 264/296; 264/322; 264/331.14; 264/342 R; 264/127; 425/174.2; 623/1; 623/901
[58] Field of Search ............. 264/23, 68, 230, 235, 264/288.8, 289.6, 296, 322, 331.14, 342 R, 346, 130, 127; 425/174.2; 623/1, 901

[56] References Cited

U.S. PATENT DOCUMENTS

| | | | |
|---|---|---|---|
| 3,953,566 | 4/1976 | Gore | 264/288.8 X |
| 3,962,153 | 6/1976 | Gore | 521/79 |
| 4,297,306 | 10/1981 | Yoshino et al. | 264/23 |
| 4,321,711 | 3/1982 | Mano | 623/1 |
| 4,647,416 | 3/1987 | Seiler, Jr. et al. | 264/118 |

Primary Examiner—Jeffery Thurlow
Assistant Examiner—Leo B. Tentoni

[57] ABSTRACT

PTFE vascular tubing is guided on to a tapered ultrasonic horn as the horn is oscillating at a high frequency. This action causes the end of the tubing moved onto the horn to expand. The expanded tubing is then positioned on a mandrel having a desired shape, such as tapered, and resintered. The finished tubing with an expanded diameter on one end and a non-expanded diameter on the other end is then removed from the mandrel, and is ready for use. Untapered tubing can also be radially expanded by this method to provide a thinner wall.

16 Claims, 2 Drawing Sheets

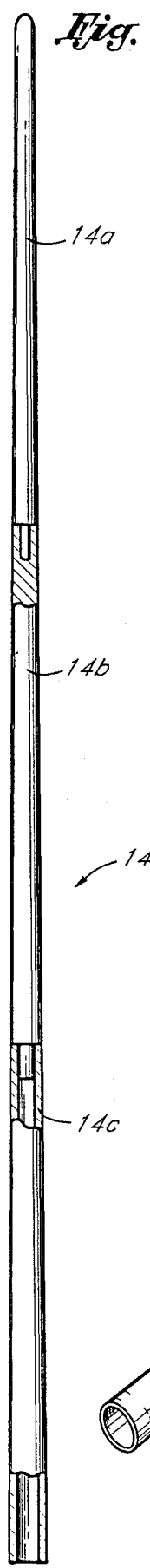
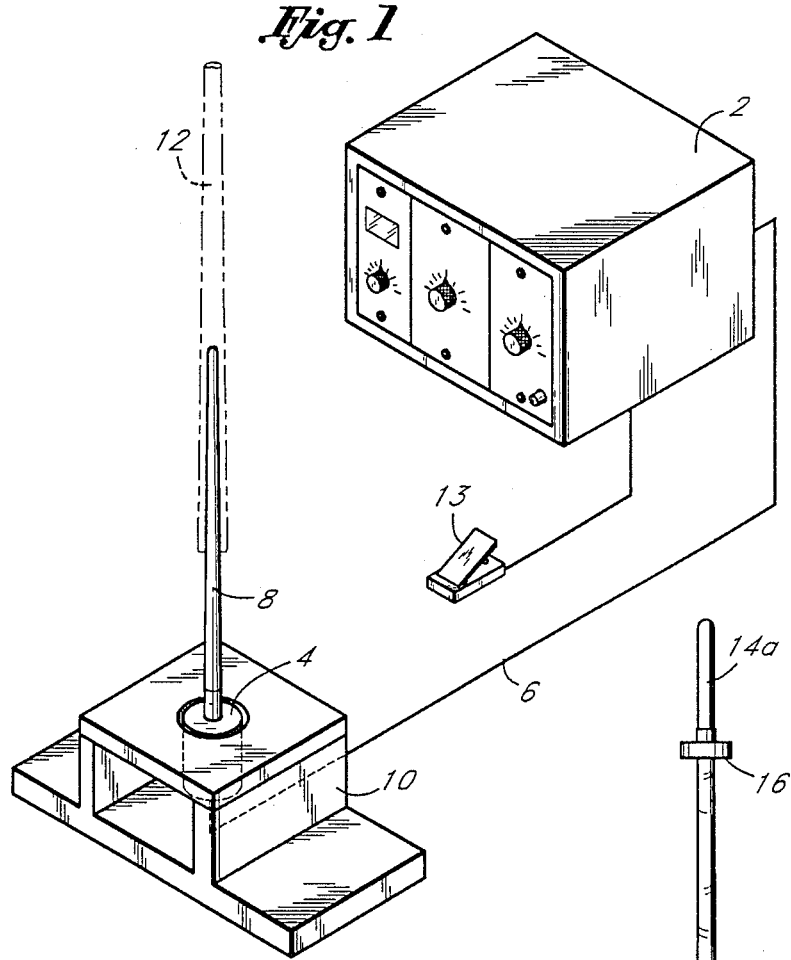
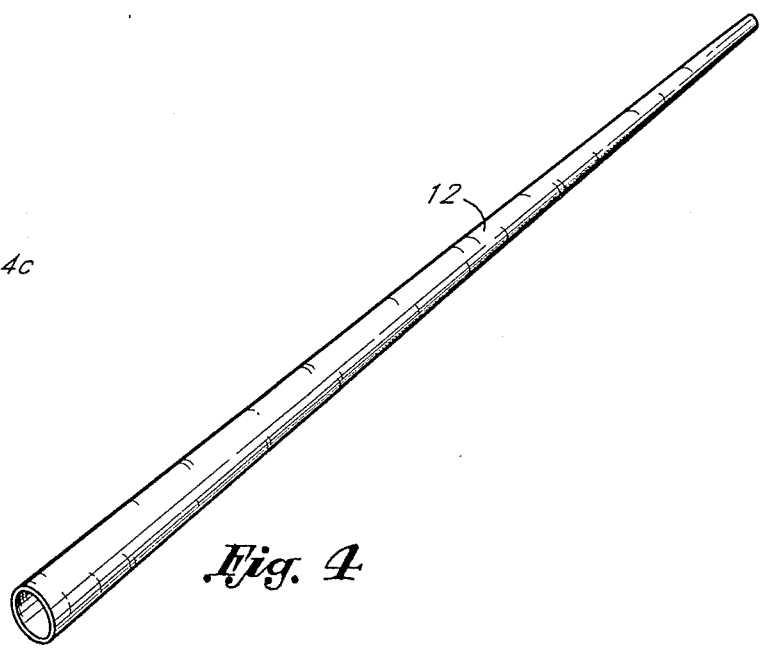
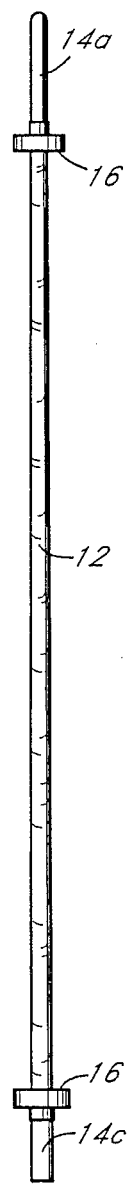

4,957,669

METHOD FOR PRODUCING TUBING USEFUL AS A TAPERED VASCULAR GRAFT PROSTHESIS

FIELD OF THE INVENTION

This invention relates to a method of providing axially stretched tapered or stepped, or thin wall tubes particularly for use as synthetic vascular graft prostheses. The invention is particularly useful with polytetrafluoroethylene (PTFE) tubing that has been stretched to create a uniformly porous structure.

BACKGROUND OF THE INVENTION

As the diameter of blood vessels varies from individual to individual, as well as within the individual, it is desirable to have a vascular graft prosthesis tube which has a diameter on one end larger than the other, and preferably has an axially tapered or stepped diameter The varying diameter of the tube provides the surgeon with a variety of different diameters of prosthesis from which to match to the size of the blood vessel being replaced One of the common applications for vascular graft prostheses is in an arterial-venous fistula or shunt from an artery to a vein for patients who require hemodialysis. When the arterial-venous fistula is in place, the capillaries which ordinarily serve as the transition from the artery to the vein are bypassed. The radial artery, which transports blood to the hands, is typically used in the arterial-venous fistula procedure.

One of the difficulties encountered during the arterial-venous fistula procedure is the "steal" syndrome, whereby too much blood flows through the fistula or shunt and insufficient amounts of blood arrive at the extremity, e.g., the hands. Utilizing a vascular graft prosthesis which is longitudinally tapered providing a smaller diameter at one end gradually increasing to a larger diameter at the other end, decreases the amount of blood flowing through the vascular graft prosthesis and thereby increases the blood flow to the extremity.

In view of the foregoing, a method for providing a tapered vascular graft prosthesis is desired In some situations it may also be desirable to provide tubing which has a thinner wall.

SUMMARY OF THE INVENTION

In accordance with the invention, an untapered flexible tubing made of PTFE or similar material is positioned on an elongated ultrasound horn which is tapered on a free end. The tubing is moved onto the horn while the horn is energized causing the tube to vibrate. The vibration of the horn at a high frequency stretches the tubing and generates heat so that the tubing is easily moved onto the horn. Preferably this process is facilitated by applying a lubricant to the tubing before placing the tubing on the horn. After the desired amount of tubing is positioned on the horn, the horn is deactivated, and the tubing is maintained on the deactivated horn for a predetermined period of time in order to allow it to cool.

If tapered tubing is desired, the placing of the tubing on the horn is interrupted while there is still tubing on the tapered portions of the horn. If tubing with an enlarged, thinner wall without a taper is desired, a quantity of tubing is placed totally onto the larger diameter end of the horn.

The horn is then briefly re-energized to facilitate removal of the tubing from the horn. The tubing is placed on a mandrel of a desired shape and the ends are restrained to prevent axial shrinking. The tubing is then sintered at a temperature approximately equal to or less than the crystalline melting point of the material, which thermally sets the tubing material and causes it to take the shape of the mandrel.

BRIEF DESCRIPTION OF THE DRAWINGS

FIG. 1 schematically shows an ultrasound horn and a power supply with a vascular graft prosthesis tube shown inserted over the horn in phantom outline.

FIG. 2 is an elevational, partially sectioned view of the mandrel.

FIG. 3 is a schematic view of the tube axially restrained on a mandrel.

FIG. 4 shows a completed tapered graft prosthesis.

DESCRIPTION OF THE PREFERRED EMBODIMENTS

Figure 5:
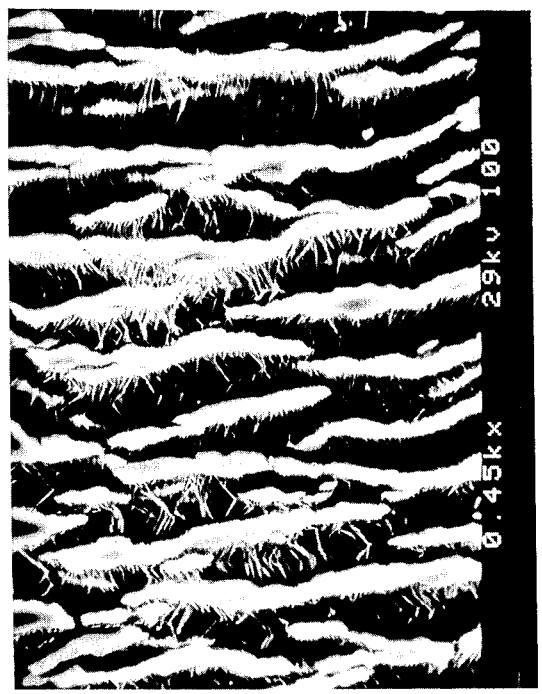
FIG. 5 is a photomicrograph of the radially expanded tubing.

The vascular graft prostheses are typically made from those polymeric materials capable of being sterilized and suitable for long-term use in contact with, and transportation of, blood within the human body. The typical polymeric materials have the property of becoming porous when stretched at temperatures less than their melting temperatures. Porosity is desired to permit tissue in growth from the outside, and to nourish the neointima that forms on the inside surface. On the other hand, the wall must not be so porous as to continually leak blood. Typically, the tubing is made by the paste extrusion method, and is then axially stretched 2 to 6 times the original length to become porous, and heat set while axially restrained. The preferred polymer is highly crystalline PTFE (less than about 2% amorphous). In one form of desirable PTFE tubing, circumferential ribs are formed on the exterior of the tube to resist collapse of the tube when bent. However, ribbed tubes can be made from other polymers with significant crystallinity, such as nylon, polyester, and polypropylene. The vascular graft tubes are cylindrical in form and range in size from about 1.0 mm to about 36 mm inside diameter, with a wall thickness of about 0.5 mm to about 2.0 mm. A method of making stretched, ribbed tubing is described in U.S. Patent No. 4,647,416—Seiler, et al., which is incorporated herein by reference. That patent refers to other patents describing methods of making porous tubing for vascular grafts. One commercial example of a satisfactory tubing made by the process of the Seiler patent is that sold under the trademark TETRAFLEX by Shiley Incorporated of Irvine, Calif.

Referring to FIG. 1, there is shown ultrasound equipment including a power supply 2 equipped with an amplitude control device. Typical suitable power supplies have an output of 40 kHz and 150 to 700 watts; and 20 kHz and 150 to 3200 watts. The ultrasound equipment further includes a booster horn 4 which is connected to the positive end 6 of the power supply and an elongated ultrasound horn 8 having a tapered free end. The horn 8 should have a length suitable for the expanding application. It is believed that the horn should suitably be about 1 to 6 wavelengths, in half wave length increments of the ultrasound waves to be applied. However, horns are under development for longer grafts. A housing 10 holds the booster horn and the ultrasonic horn in place. A section of tubing 12 is schematically shown on the horn 8. A foot operated switch 13 conveniently controls the power supply, while leaving the hands free to manipulate the tubing.

The standard manufacturing process for the PTFE tube 12 is normally concluded with a heat treatment at temperatures of approximately 325° to 450°C. (sintering), while restraining the tube walls from axial shrinkage. In order to utilize the present method invention, the PTFE tubing should be in the 60% to 100% sintered condition, in order to provide adequate strength As the first step of the method of the present invention, the vascular graft prosthesis tube 12 is dipped into a lubricant or facilitating liquid to about ⅓ to ⅔ the length of the tube, or the entire length of the tubing is coated if a non-typical thin wall tubing is to be made. Paint thinner or mineral spirits sold under the brand name ISOPAR H has been found to be a satisfactory material for the intended purpose. The power supply 2 is then activated and the tube 12 is pulled or guided slowly over the tapered tip of the ultrasonic horn to the length desired. The horn 8 primarily oscillates axially. Hence this movement of the tube 12 in being guided onto the tapered mandrel rapidly applies radially expanding forces to the tubing. This action expands the tube and produces heat, which further facilitates the expansion.

It is believed that the theory behind the stretching process is that the ultrasonic waves are transmitted through the horn as mechanical energy. This mechanical energy, plus the rapid pulsing of the sound waves produces heat, plus a stress relieving characteristic or phenomena, which allows the tubing to be guided or fed easily over the expanding horn.

After a desired length of tubing has been moved onto the horn, the horn is deactivated for a period of approximately 10 to 30 seconds to permit the PTFE tubing to cool and set. The horn is then re-energized briefly to loosen the tubing with respect to the horn so that it can be readily removed from the tapered end of the horn.

The PTFE tubing 12, which has been expanded on the horn, is then placed on a stepped or tapered mandrel 14 which is approximately the same size or else smaller than the horn.

Although a one piece mandrel may be employed, a prototype version was made of three sections, a solid, straight tip section 14a, coupled to a solid tapered section 14b, coupled to a straight hollow or tubular section 14c, as seen in FIG. 2. The tubular structure of section 14c is desirable from the standpoint of reducing heating and cooling times. Having the small diameter straight section separable from the tapered section is convenient for different expansions of a given size. That is, a 6 mm section 14a might be coupled to an 8, 10 or 12 mm diameter tubular straight section 14c by a tapered section 14b which tapers from 6 mm to 8, 10 or 12 mm. The different sections are preferably press fit together and then silver brazed and polished.

For making untapered thin wall tubing, the straight large diameter mandrel section 14c of the desired length is employed.

Each end of the PTFE tubing is secured on the mandrel, typically with suitable clamps 16 to restrain it from axial shrinkage, as seen in FIG. 3. The tube 12 is then resintered just below the crystalline melting point of the PTFE tubing to provide the tubing a new "memory" in its expanded shape. The exact sintering temperature will depend on the composition of the PTFE tubing utilized, but is in the range of 325° to 450°C. The resintering process requires approximately 3 to 10 minutes. The tubing can then be removed from the mandrel, and it is ready for use.

If thin walled, non-tapered tubing is desired, tubing expanded throughout its length by the horn is placed on a non-tapered mandrel having the desired diameter. Further, in making tapered tubing the entire length of tubing may be expanded on the horn, and then placed on a tapered mandrel. The tubing, when heat treated on the mandrel, shrinks to the mandrel shape. It should be recognized that using the expansion technique described herein, thin walls can be obtained that cannot be obtained directly through extrusion, as is used in initial fabrication of the tubing.

A preferred method of the invention is illustrated by the following example. A length of circumferentially ribbed, porous TETRAFLEX PTFE tubing was selected having an inner diameter of 6 mm, and a wall thickness of 0.075 mm. The horn had a semi-spherical tip with a radius of about 1/16 inch (about 1.5 mm) and tapered in an axial length of 3 inches from ⅛-inch diameter (about 3 mm) to a ⅜-inch diameter (about 9 mm). The overall length of the horn 8, corresponding to 2 times the wavelength of the sound waves applied, was about 12 inches, with a 3 inch tapered tip and 9 inches untapered. The horn was solid, being made of a titanium alloy type 6-4, having about 6 parts aluminum, 4 parts vanadium to 90 parts titanium. Horns can also be made of type 7-4 Ti or 7075 T6 aluminum. The horn was activated by standard a 40 kHz, 700 watt power supply, acquired from Branson Ultrasonics Corporation of Danbury, Conn. A booster horn is also available from this company. The tubing was coated with ISOPAR H and pulled or guided slowly over the tapered tip of the horn onto the non-tapered portion, to the extent desired (as generally illustrated in FIG. (1). A desired length of tubing was moved onto the activated horn in about 10 seconds, following which the horn was deactivated. The expanded tubing was then allowed to cool about 10 seconds. The horn was then reactivated momentarily, and the tubing removed. Lintless cotton cloth was used to handle the heated tubing.

The expanded tubing was then placed onto a tapered mandrel (as generally illustrated in FIG. 2) made of type 316 stainless steel. Types 321, 323 and 347 are also acceptable. The mandrel was formed of three sections, a straight tip section 14a about 13 inches in length with a tip diameter of about 6 mm, a main tapered section 14b about 40 cm (15.75 inches) in length tapering from 6 mm to 8 mm on its large end, and a non-tapered, tubular section 14c about 13 inches, with a wall thickness of about 0.070 inches. The ends of the tubing were restrained by clamps (as generally illustrated in FIG. 3) and the tubing heated to a sintering temperature of about 375°C. for 5 minutes, and then removed. It should be noted that the tubing in the example was stretched to a diameter larger than the mandrel large diameter section. During the sintering step, the tubing shrank radially to the size of the mandrel.

In another example, the tapered section was only about 1½ inches. A stepped transition section instead of tapered has also been tested. A stepped tube may be desirable in some instances.

Below is a table indicating characteristics of well known, standard 6 mm graft compared to that of three initial prototype samples of the tubing radially expanded to 12 mm. It is interesting to note that the density and the axial tensile strength of the expanded tubing is greater than the standard even though wall thickness is much thinner Also somewhat surprisingly, pore size is slightly smaller with the expanded tubing and correspondingly water permeation pressure is slightly higher. The ability or strength of the material to withstand suturing to the patient's vessels appears to be satisfactory.

TABLE I

PROPERTIES OF AXIALLY EXPANDED TETRAFLEX GRAFT SPECIMENS VS. STANDARD 6 MM GRAFTS

| PROPERTY | MEAN VALUE STANDARD 6 MM GRAFT | MEAN VALUE AXIALLY EXPANDED (6-12 MM) GRAFT |
|---|---|---|
| Density (8 mm/cc) | 0.57 | 0.72 |
| Tensile Strength Radial (dyn/mm$_2$) | 7.20 | 5.26 |
| Tensile Strength Longitudinal (dyn/mm$_2$) | 8.50 | 15.19 |
| Wall Thickness (mm) | 0.55 | 0.16 |
| Fibril Length ($\mu$m) | 15.80 | 18.25 |
| Pore Size ($\mu$m) | 4.90 | 4.17 |
| Water Permeation Pressure (mm/Hg) | 289.00 | 392.00 |
| Burst Strength (30 psi/60 sec) min. | Passed | Passed |

The photomicrograph of FIG. 5 is a plan view of radially expanded ribbed TETRAFLEX tubing showing a wall section between the ribs. The radial expansion is in the top to bottom direction of the page. The generally horizontal lines are the nodes of the material joined by the generally vertical fibers or fibrils of the material. The dark areas are the pores or spaces between the fibrils and nodes.

While the invention has been described in the context of a vascular prosthesis and as a method of making such an item, the tubing may be useful in other medical applications, as well as outside the medical field.

I claim:

1. A method for expanding flexible tubing useful for making a vascular prosthesis tubing including the steps of:
    energizing an elongated ultrasound horn having a free end which increases from a cross-section smaller than an internal cross-section of said tubing to a cross-section larger than the internal cross-section of the tubing;
    placing an end of said tubing on the free end of said horn and guiding said tubing further onto said horn as the horn is vibrating, whereby a portion of said tubing moved onto the larger cross-section of the horn is expanded in cross-section;
    de-energizing said horn after said tubing has been expanded;
    maintaining said tubing on said horn for a predetermined time period to allow the expanded tubing portion to cool in its expanded state;
    removing said tubing from the horn and placing it on a mandrel;
    restraining the ends of said tubing in a manner to prevent the tubing from shrinking axially; and
    sintering said tubing for a predetermined time at a temperature sufficient to cause the expanded tubing to shrink radially to the shape of the mandrel and to maintain such shape when removed from said mandrel.

2. The method of claim 1, including removing said tubing from said horn while briefly re-energizing the horn to facilitate removal of the tubing.

3. The method of claim 1, wherein said placing includes placing the tubing on an untapered mandrel so as to form non-tapered, thin wall tubing.

4. The method of claim 1, including applying a to said tubing before placing the tubing on the horn.

5. The method of claim 1, wherein said energizing step is performed in a manner to cause said horn to oscillate axially at a high frequency.

6. A method for expanding flexible tubing useful for making a vascular prosthesis tubing including the steps of:
    energizing an elongated ultrasound horn having a free end which increases from a cross-section smaller than an internal cross-section of said tubing to a cross-section larger than the internal cross-section of the tubing;
    placing an end of said tubing on the free end of said horn and guiding said tubing further onto said horn as the horn is vibrating, whereby a portion of said tubing moved onto the larger cross-section of the horn is expanded in cross-section;
    removing said tubing from said horn;
    placing said tubing on a tapered mandrel;
    securing each end of said tubing; and
    sintering said tubing for a predetermined time.

7. The method of claim 6, wherein said energizing step is performed with a horn having a length greater than a wavelength of ultrasound energy applied to the horn.

8. The method of claim 7, wherein said energizing step is performed with a horn having a length of from about 1 to 6 wavelengths, in half wavelength increments, of said energy.

9. The method of claim 6, wherein said sintering is performed by heating said tubing to approximately 325° to 450°C. for a period of from three to ten minutes.

10. The method of claim 6, including dipping said tubing in a liquid for facilitating feeding the tubing on said horn.

11. The method of claim 6, wherein said energizing step is performed with a 40 kHz, 700 watt power supply.

12. The method of claim 6, wherein said energizing step is performed with a 20 kHz, 3200 watt power supply.

13. The method of claim 6, wherein said tubing is made of PTFE.

14. A method for expanding tubing useful as a vascular prosthesis, comprising the steps of:
    energizing an elongated ultrasound horn having a tapered free end which increases from a diameter smaller than an internal diameter of said tubing to a diameter larger than the internal diameter of said tubing;
    dipping a portion of said tubing into a liquid;
    placing an end of said tubing portion on said free end of said horn and guiding said tubing further onto the horn, as the horn is axially vibrating, whereby said tubing is radially expanded;
    de-energizing said horn;
    maintaining said tubing on said horn for a predetermined time to allow the expanded tubing portion to cool and set in an expanded state;
    removing said tubing from said horn while briefly re-energizing the horn to facilitate removal;

placing said expanded tubing on a mandrel;
restraining the tubing from axial shrinkage; and
sintering said tubing for a predetermined time period so as to cause the tubing to shrink to and maintain the shape of the mandrel.

15. the method of claim 14, wherein said energizing step is performed with a 40 kHz, 700 watt power supply.

16. The method of claim 14, wherein said energizing step is performed with a horn having a length of from about 1 to 6 wavelengths, in half-wavelength increments, of ultrasound energy applied to said horn.

* * * * *